US00PP08724P

United States Patent [19]

van Andel

[11] Patent Number: Plant 8,724

[45] Date of Patent: May 10, 1994

[54] SPRAY CARNATION NAMED STAGIGI

[75] Inventor: Jacob van Andel, Aalsmeer, Netherlands

[73] Assignee: Van Staaveren B.V., Aalsmeer, Netherlands

[21] Appl. No.: 780,141

[22] Filed: Oct. 21, 1991

[51] Int. Cl.[5] ..... A01H 5/00

[52] U.S. Cl. ..... Plt./70.2

[58] Field of Search ..... Plt. 70.2, 70.6, 70.1

*Primary Examiner*—Howard J. Locker

*Attorney, Agent, or Firm*—Tilton, Fallon, Lungmus & Chestnut

[57] ABSTRACT

A new spray carnation variety particularly distinguished by its profuse production of small flowers the petals of which are white at the base and purple to the outer edge the flowers being carried on strong, upright stems and arranged in a cluster drawing from the upper end of the main stem of medium height; the plant itself being a vigorous, fast growing bush of medium height with a moderate amount of foliage.

1 Drawing Sheet

BACKGROUND OF THE NEW PLANT

This new spray carnation cultivar originated as a hybrid seedling developed by me at our nursery in Aalsmeer, Holland, by crossing two carnation varieties, *Dianthus superbus* and *Dianthus superbus* (both unpatented) selected from my collection of carnation varieties maintained at our Aalsmeer nursery for breeding purposes. The female parent of Stagigi is a unnamed *Dianthus superbus* cultivar, and is characterized by a widely branched spray and white flowers with deep incisions. The male parent is a unnamed *Dianthus barbatus* cultivar, and is characterized by a more compact spray and small white flowers with straight margins. The cultivar Stagigi is a true hybrid between the two botanical species. This seedling was selected for propagation because of its very unusual flower coloring and its sturdy, fast growing growth habit. Under my direction, propagation was done by means of cuttings. The initial success of the propagation was continued through several successive generations which proved that the new variety retained all of the distinguishing characteristics of the original parent seedling and that these characteristics hold true from generation to generation and appear to be firmly fixed.

DESCRIPTION OF THE DRAWING

This new carnation cultivar is illustrated by the accompanying photographic drawing which, in full color, shows the distinguishing color characteristics and flower form of this plant, the color rendition being as nearly true as is reasonably possible to obtain by conventional photographic procedures.

DESCRIPTION OF THE NEW PLANT

The following is a detailed description of my new carnation plant based upon observation of plants grown in greenhouses at Aalsmeer, Holland with color designations according to The R.H.S. Colour Chart of The Royal Horticultural Society of London, England.

THE PLANT

Origin: Seedling.

Parentage:

*Seed parent.*—*Dianthus superbus* (unpatented).

*Pollen parent.*—*Dianthus barbatus* (unpatented).

Classification:

*Botanic.*—Dianthus Hybrid.

*Commercial.*—Spray carnation.

Form: Strong erect bush having at least four stems emitted near the ground.

Height: About 60 cm.

Cane length: About 60 cm. depending on season.

Branching character: The main stem has 2–4 side branches each. The side branches have 1–2 side branches each.

Growth: Vigorous, upright with moderate strength producing flowers within three to four months from planting.

Foliage:

*Quantity.*—Moderate.

*Number of leaves.*—16–20.

*Size of leaf.*—About 11 cm. long and 3 cm. wide.

*Shape.*—Oval.

*Texture.*—Leathery.

*Color.*—Upper side — RHS 137A. Under side — RHS 137C.

*Ribs and veins.*—Hardly noticeable.

*Rachis.*—Hardly noticeable.

THE BUD

Size:

*Diameter.*—Between approximately 0.4 and 0.5 cm.

*Length.*—Between approximately 2 and 2.5 cm.

Form: Cylindrical.

Rate of opening: Normal.

Color:

*When sepals first divide.*—74-B.

*When petals begin to unfurl.*—74-B.

Sepals:

*Number.*—Usually 5.

*Character.*—The sepals are hooded over the bud before dividing and stand up as the flower petals unfurl. The sepals are joined together at the lower part and are sharply pointed at the apex.

Calyx:

*Shape.*—Cylindrical.

*Size.*—About 0.5 cm. broad and 2.5 cm. long.

*Aspect.*—Smooth.

*Splitting.*—None color: RHS 139C.

Flower stem:

*Length.*—About 60 cm.
*Character.*—Erect.
*Color.*—Dark green.

THE FLOWER

Blooming habit: Recurrent and profuse.
Flower size: Small.
*Diameter.*—About 2.5 to 3 cm.
*Depth.*—About 0.5 cm.
Borne: In a tightly grouped cluster.
Shape:
*When bloom first opens.*—Flat.
*When bloom matures.*—Flat. Number of flowers per main flower stem: 10–16.
Petalage:
*Number of petals.*—5.
*Arrangement.*—Imbricated.
*Form.*—Fan-shaped with deeply serrated edges.
*Texture.*—Soft.
*Appearance.*—Velvety.
*Color.*—Outer petal — 74-B. Base — 77-D. Reverse side — 75-A. Central Mottled Portion: The color of the central "mottled" portion of the petal is RHS 74-A and in this part there are 30–50 small spots with the color RHS 73-A.
Fragrance: Slight.

Discoloration after full bloom: Slight.
Persistance: The petals hang on and dry.
Disease resistance: Good resistance to *Fusarium oxysporum* as observed at the Horticultural Experimental Station of Aalsmeer, Holland.
Lasting Quality:
*On plant.*—About 21 days.
*As a cut flower.*—About 15 days.

THE REPRODUCTIVE ORGANS

Stamens:
*Number.*—Approximately 10.
*Anthers.*—Size: Approximately 2 mm. Color: Pink.
*Filaments.*—Length: About 2.5 cm. Color: White.
Pistils:
*Number.*—1.
*Styles.*—Length: Approximately between 2 and 2.5 cm. Color: White.
*Stigmas.*—Color: Purple.

I claim:

1. A new and distinct spray carnation plant substantially as herein shown and described, characterized by its recurrent, profuse production of small flowers which are white at the base and purple to the outer edge.

* * * * *

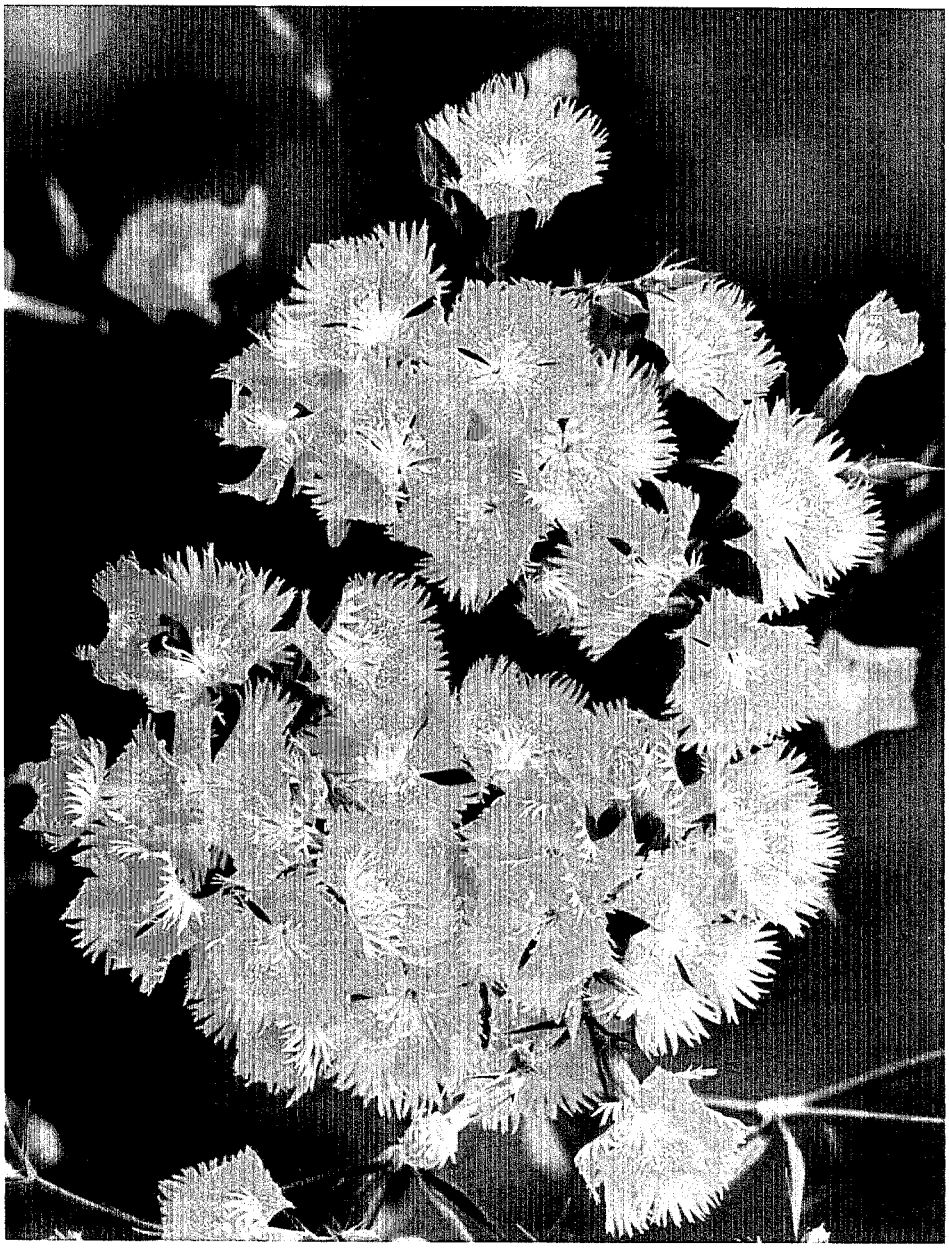

UNITED STATES PATENT AND TRADEMARK OFFICE

CERTIFICATE OF CORRECTION

PATENT NO. : Plant 8,724
DATED : May 10, 1994
INVENTOR(S) : van Andel

It is certified that error appears in the above-indentified patent and that said Letters Patent is hereby corrected as shown below:

Column 1, line 6, delete "Dianthus superbus and Dianthus superbus" and insert -- Dianthus superbus and Dianthus barbatus --

Signed and Sealed this

Second Day of May, 1995

Bruce Lehman

*Attest:*

BRUCE LEHMAN

*Attesting Officer*

*Commissioner of Patents and Trademarks*